US00PP19449P2

(12) United States Plant Patent
Akerboom

(10) Patent No.: US PP19,449 P2
(45) Date of Patent: Nov. 18, 2008

(54) *ASTER* PLANT NAMED 'BLUE DIAMOND'

(50) Latin Name: *Aster hybrida*
Varietal Denomination: Blue Diamond

(75) Inventor: Petrus J. Akerboom, Ter Aar (NL)

(73) Assignee: NachtVlinder B.V., Ter Aar (NL)

( * ) Notice: Subject to any disclaimer, the term of this patent is extended or adjusted under 35 U.S.C. 154(b) by 0 days.

(21) Appl. No.: 11/881,794

(22) Filed: Jul. 27, 2007

(51) Int. Cl.
*A01H 5/00* (2006.01)

(52) U.S. Cl. ..... Plt./355

(58) Field of Classification Search ..... Plt./355
See application file for complete search history.

*Primary Examiner*—Kent L. Bell
*Assistant Examiner*—June Hwu
(74) *Attorney, Agent, or Firm*—C. A. Whealy

(57) ABSTRACT

A new and distinct cultivar of *Aster* plant named 'Blue Diamond' characterized by its uniform, upright and strong flowering stems; uniform and freely flowering habit; and decorative-type inflorescences with violet-colored ray florets.

3 Drawing Sheets

Botanical designation: *Aster hybrida.*
Cultivar denomination: 'Blue Diamond'.

BACKGROUND OF THE INVENTION

The present invention relates to a new and distinct cultivar of *Aster* plant, botanically known as *Aster hybrida* and hereinafter referred to by the name 'Blue Diamond'.

The objective of the breeding program is to create new cut flower-type *Aster* cultivars with uniform plant growth habit, strong flowering stems, large decorative inflorescences and attractive ray floret colors.

The new *Aster* originated from a cross-pollination in July, 2002 in Ter Aar, The Netherlands of a proprietary selection of *Aster hybrida* identified as code number Nvlgr 99123, not patented, as the female, or seed, parent with a proprietary selection of *Aster hybrida* identified as code number Nvlgr 99240, not patented, as the male, or pollen, parent. The new *Aster* was discovered and selected by the Inventor as a single flowering plant within the progeny of the stated cross-pollination in a controlled environment in Ter Aar, The Netherlands in July, 2003.

Asexual reproduction of the new *Aster* by vegetative cuttings was first conducted in Ter Aar, The Netherlands in August, 2003. Asexual reproduction by cuttings has shown that the unique features of this new *Aster* are stable and reproduced true to type in successive generations.

SUMMARY OF THE INVENTION

Plants of the cultivar Blue Diamond have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Blue Diamond'. These characteristics in combination distinguish 'Blue Diamond' as a new and distinct cut flower *Aster* cultivar:

1. Uniform, upright and strong flowering stems.
2. Uniform and freely flowering habit.

3. Decorative-type inflorescences with violet-colored ray florets.

Plants of the new *Aster* differ from plants of the parent selections in the following characteristics:

1. Plants of the new *Aster* have larger inflorescences than plants of the parent selections.
2. Plants of the new *Aster* and the parent selections differ in ray floret coloration.
3. Inflorescences of plants of the new *Aster* have more ray florets than inflorescences of plants of the parent selections.

Plants of the new *Aster* can be compared to plants of the *Aster* cultivar Milka, disclosed in U.S. Plant Pat. No. 10,602. In side-by-side comparisons conducted in Ter Aar, The Netherlands, plants of the new *Aster* differed from plants of the cultivar Milka in the following characteristics:

1. Plants of the new *Aster* had thicker flowering stems than plants of the cultivar Milka.
2. Plants of the new *Aster* had larger inflorescences than plants of the cultivar Milka.
3. Inflorescences of plants of the new *Aster* had more ray florets than inflorescences of plants of the cultivar Milka.

BRIEF DESCRIPTION OF THE PHOTOGRAPHS

The accompanying photographs illustrate the overall appearance of the new *Aster.* These photographs show the colors as true as it is reasonably possible to obtain in colored reproductions of this type. Colors in the photographs may differ slightly from the color values cited in the detailed botanical description which accurately describe the colors of the new *Aster.*

The photograph on the first sheet comprises a side perspective view of a typical flowering plant of 'Blue Diamond'.

The photographs on the second sheet is a close-up view of the upper portion of a typical flowering stem of 'Blue Diamond'.

The photograph on the third sheet is a close-up view of a typical inflorescence of 'Blue Diamond'.

DETAILED BOTANICAL DESCRIPTION

The aforementioned photographs and following observations and measurements describe plants grown from September to April in Ter Aar, The Netherlands in ground beds in a glass-covered greenhouse and under conditions and practices which approximate those generally used in commercial container *Aster* production. During the production of the plants, day temperatures ranged from 18° C. to 35° C. and night temperatures ranged from 12° C. to 18° C. Plants used in the photographs and for the description were about eight months old. In the following description, color references are made to The Royal Horticultural Society Colour Chart, 1995 Edition, except where general terms of ordinary dictionary significance are used.

Botanical classification: *Aster hybrida* cultivar Blue Diamond.

Parentage:

*Female, or seed, parent.*—Proprietary selection of *Aster hybrida* identified as code number Nvlgr 99123, not patented.

*Male, or pollen, parent.*—Proprietary selection of *Aster hybrida* identified as code number Nvlgr 99240, not patented.

Propagation:

*Type.*—Terminal vegetative cuttings.

*Time to initiate and develop roots, summer.*—About 16 to 19 days at temperatures of about 22° C.

*Time to initiate and develop roots, winter.*—About 21 to 26 days at temperatures of about 18° C.

*Root description.*—Moderately thick, fibrous; white in color.

*Rooting habit.*—Moderate branching; medium density.

Plant description:

*Appearance.*—Herbaceous decorative-type cut flower *Aster.* Upright plant habit; narrow inverted triangle with lateral branches somewhat outwardly spreading. Strong and freely branching growth habit with about twelve primary lateral branches. Moderately vigorous growth habit.

*Plant height.*—About 100 cm.

*Plant width.*—About 42 cm.

*Lateral branches.*—Length: About 19.2 cm. Diameter: About 2 mm. Internode length: About 2.9 cm. Strength: Strong. Texture: Smooth, glabrous. Color: 143A; longitudinal stripes, 144B.

Foliage description:

*Arrangement.*—Alternate, simple; sessile.

*Length.*—About 12.7 cm.

*Width.*—About 2 cm.

*Shape.*—Lanceolate.

*Apex.*—Acute.

*Base.*—Cuneate.

*Margin.*—Finely serrate.

*Texture, upper and lower surfaces.*—Smooth, glabrous.

*Color.*—Developing foliage, upper surface: Close to 137A. Developing foliage, lower surface: Close to 137A to 137B. Fully expanded foliage, upper surface: Between 137A and 147A; venation, 144A. Fully expanded foliage, lower surface: Close to 137B; venation, between 143B and 144A.

Inflorescence description:

*Appearance.*—Decorative-type inflorescence form with oblanceolate-shaped ray florets. Inflorescences borne on terminals above and beyond the foliage. Disk and ray florets arranged acropetally on a capitulum. Inflorescence not fragrant.

*Flowering response.*—Under natural conditions, plants flower continuously from late September to late October in The Netherlands. Inflorescences not persistent. Inflorescences last about three weeks on the plant and about two weeks as a cut flower.

*Quantity of inflorescences.*—Freely flowering, about 240 inflorescences develop per plant.

*Inflorescence bud.*—Height: About 8 mm. Diameter: About 5 mm to 1.8 cm. Shape: Flattened globular. Color: Close to 137A.

*Inflorescence size.*—Diameter: About 4.1 cm. Depth (height): About 1.9 cm. Diameter of disc: Disc florets have not been observed. Receptacle height: About 9 mm. Receptacle diameter: About 1.9 cm.

*Ray florets.*—Length: About 1.6 cm. Width: About 3.5 mm. Shape: Oblanceolate. Apex: Retuse to praemorse. Base: Attenuate. Margin: Entire. Texture, upper and lower surfaces: Smooth, glabrous, satiny. Orientation: Initially upright, then about 90° from vertical or perpendicular to peduncle. Number of ray florets per inflorescence: About 220 arranged in about eight whorls. Color: When opening, upper surface: Close to N88C. When opening, lower surface: Close to 85C; towards the base, 85D. Fully opened, upper surface: Close to N88C; color becoming closer to N88D with development. Fully opened, lower surface: Close to 85C; towards the base, 85D.

*Phyllaries.*—Number of phyllaries per inflorescence: About 50 arranged in about four whorls. Length: About 6 mm. Width: About 2 mm. Shape: Lanceolate. Apex: Acute. Base: Cuneate. Texture, upper and lower surfaces: Smooth, glabrous; leathery. Color, upper surface: Between 137A and 147A. Color, lower surface: Close to 137A.

*Peduncles.*—Length, terminal peduncle: About 3.9 cm. Length, fourth peduncle: About 8.1 cm. Diameter: About 1 mm. Angle: About 30° from vertical. Strength: Strong, flexible. Texture: Sparsely pubescent. Color: Close to 143A.

*Reproductive organs.*—Androecium: Not observed. Gynoecium: Pistil length: About 7 mm. Stigma shape: Bi-parted. Stigma color: Close to 150D. Style length: About 6 mm. Style color: Close to 157D. Ovary color: Close to 157D.

*Seed/fruit.*—Seed and fruit production has not been observed.

Disease pest resistance: Resistance to pathogens and pests common to *Asters* has not been observed on plants grown under commercial conditions.

Temperature tolerance: Plants of the new *Aster* have been observed to tolerate temperatures ranging from about −5° C. to about 35° C.

It is claimed:

1. A new and distinct *Aster* plant named 'Blue Diamond' as illustrated and described.

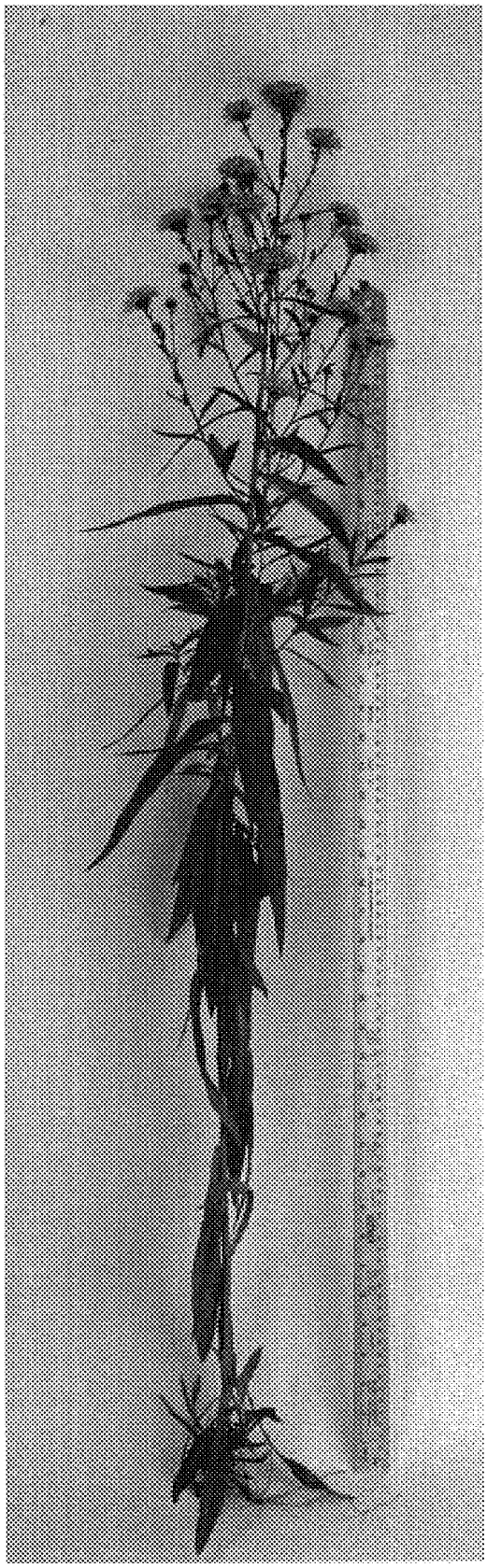

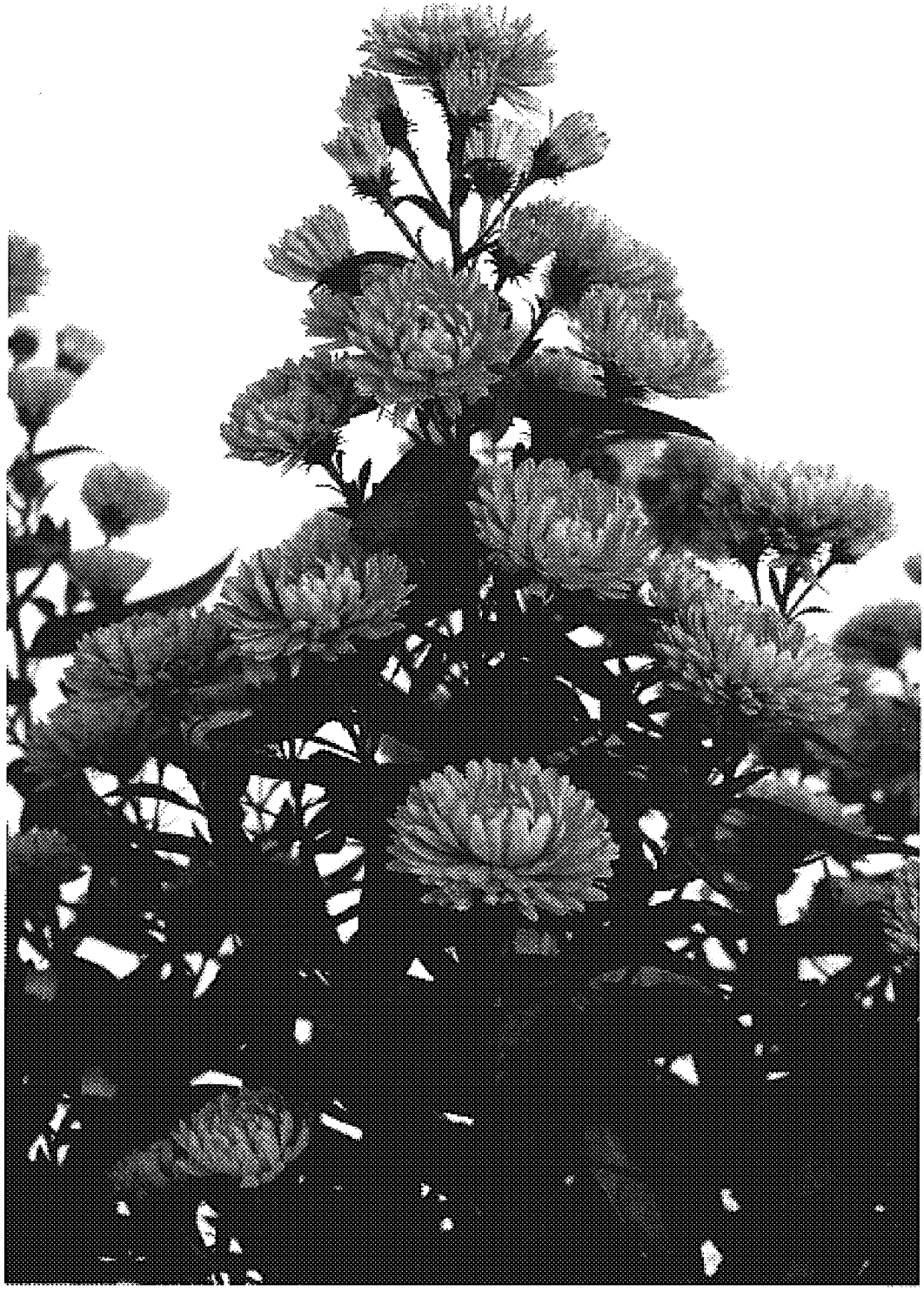

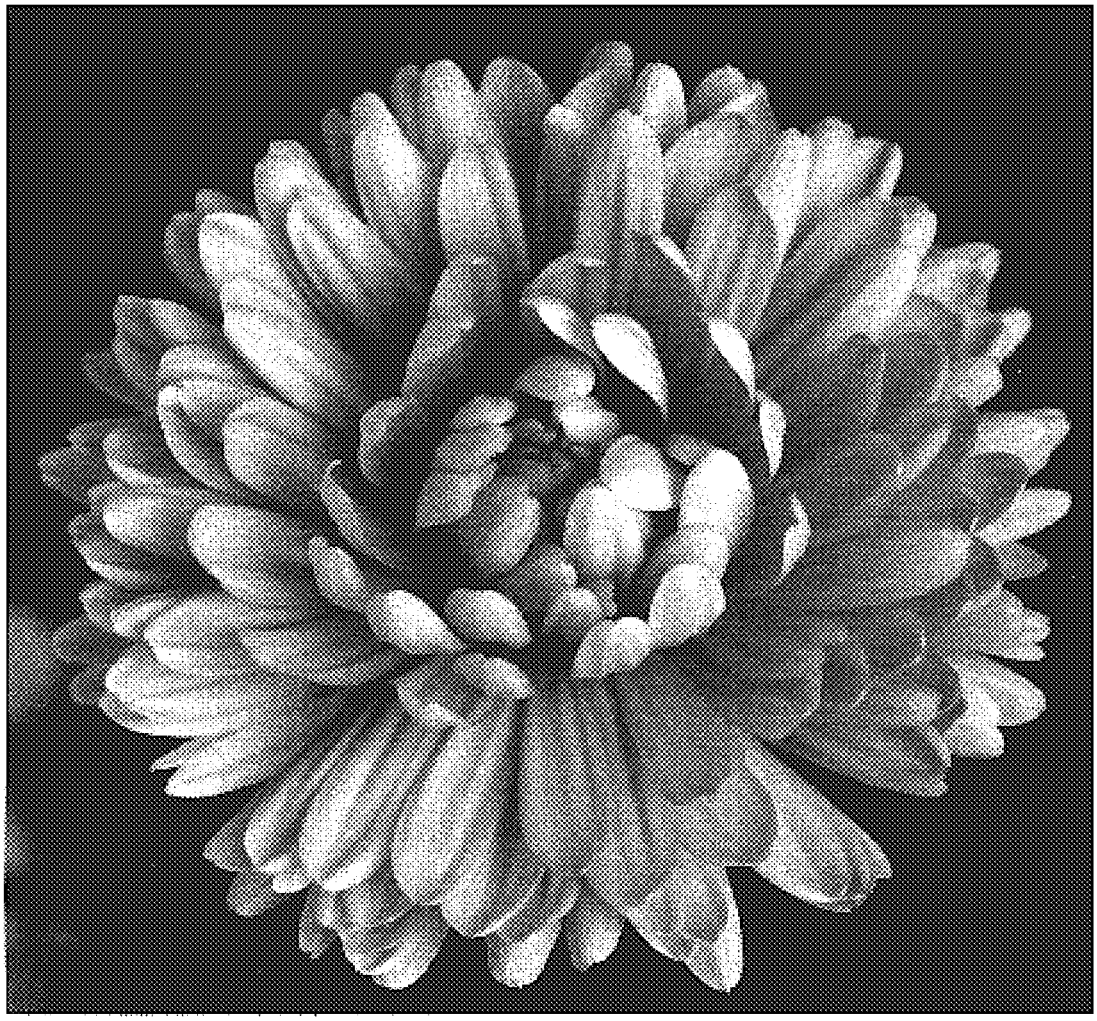

* * * * *